(12) United States Patent
Rosen et al.

(10) Patent No.: US 7,485,437 B1
(45) Date of Patent: *Feb. 3, 2009

(54) METHOD FOR DETECTING BACTERIAL ENDOSPORES IN A SEALED CONTAINER

(75) Inventors: David L. Rosen, Rockville, MD (US);
Ronald E. Meyers, Columbia, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 783 days.

This patent is subject to a terminal disclaimer.

(21) Appl. No.: 10/294,644

(22) Filed: Nov. 15, 2002

(51) Int. Cl.
*C12Q 1/24* (2006.01)
(52) U.S. Cl. ............... 435/30; 435/808; 436/48; 436/52; 436/177
(58) Field of Classification Search ........... 436/48, 436/52, 177; 73/863.51, 863.71, 863.91; 435/287.2, 30, 808; *C12Q 1/24*
See application file for complete search history.

(56) References Cited

U.S. PATENT DOCUMENTS

| | | | |
|---|---|---|---|
| 5,876,960 A | 3/1999 | Rosen | |
| 6,485,962 B1 * | 11/2002 | Tabacco et al. | 435/288.7 |
| 6,498,041 B1 * | 12/2002 | Tabacco et al. | 436/172 |
| 6,573,836 B1 * | 6/2003 | Gitis et al. | 340/603 |
| 6,599,715 B1 * | 7/2003 | Vanderberg et al. | 435/34 |
| 6,613,571 B2 * | 9/2003 | Cordery et al. | 436/48 |
| 6,838,292 B1 * | 1/2005 | Rajan et al. | 436/518 |
| 2002/0124664 A1 * | 9/2002 | Call et al. | 73/863.22 |
| 2003/0136203 A1 * | 7/2003 | Yoon | 73/864.33 |

OTHER PUBLICATIONS

Rosen et al., "Chelation Number of Teribium Dipicolinate: Effects on Photominescence Lifetime and Intensity," Applied Spectroscopy, vol. 55, No. 2, pp. 208-216 (2001).
Rosen, "Bacterial Spore Detection and Determination by Use of Terbium Dipicolintate Photoluminescence," Analytical Chemistry, vol. 69, No. 6, pp. 1082-1085 (1997).
Pellegrino et al., "Bacterial Endospore Detection Using Teribium Dipicolintate Photoluminescence in the Presence of Chemical and Biological Materials," Analytical Chemistry, vol. 70, No. 9, pp. 1755-1759 (1998).
Rosen, "Bacterial Endospore Detection Using Photoluminescence from Terbium Dipicolinate", Reviews in Analytical Chemistry, vol. 18, No. 1-2, pp. 1-21 (1999).

* cited by examiner

*Primary Examiner*—David A Redding
(74) *Attorney, Agent, or Firm*—William V. Adams; William Randolph; A. David Spevack

(57) ABSTRACT

A device for detecting bacterial endospores in a sealed container. The device has a suction tube connected to an aerosol concentrator containing a lanthanide salt solution, a suction pump engaged to the aerosol concentrator, an excitation energy source and an optical set-up for directing the excitation energy source to the lanthanide salt solution and collecting photoluminescence generated by the excited lanthanide salt solution. A method for detecting bacterial endospores is also provided.

7 Claims, 2 Drawing Sheets

METHOD FOR DETECTING BACTERIAL ENDOSPORES IN A SEALED CONTAINER

STATEMENT OF GOVERNMENT INTEREST

The invention described herein may be manufactured, used and/or licensed by or for the Government of the United States of America.

BACKGROUND OF THE INVENTION

1. Field of the Invention

This invention relates generally to particle detection and, more particularly, to detecting the presence of bacterial endospores in a sealed container.

2. Description of the Related Art

Recently, mail service within the United States has been disrupted by the spread of anthrax. Such mail service includes the United States Postal Service as well as private carriers such as Federal Express, United Parcel Service (UPS), DHL and the like. Anthrax is spread through bacterial endospores shipped through the mail or other delivery services and strikes its victim, intended or otherwise, once the mail is opened. This is because after the mail is opened, bacterial endospores are dispersed into the air where they can infect the victim either through inhalation or by contacting skin. In addition to anthrax, a bioterrorist can also spread endospores that cause other diseases such as botulism, tetanus and gas gangrene through the postal service.

Infected mail is very dangerous. To date, people who have opened the mail and some postal workers who have merely sorted unopened mail have become infected by means that are still unknown. Opened mail, however, is the most dangerous in that once the mail is opened, small air currents immediately disperse the endospores. This coupled with privacy issues encountered when handling the mail make it desirable to detect the endospores without having to actually open the mail.

Known tests for detecting bacterial contamination are usually slow and often unreliable. Serological methods use antibodies which often have large cross reactivities that can cause false alarms. Mass spectroscopy has extremely complex spectra that are difficult to analyze and could cause false alarms. DNA testing is extremely slow and expensive.

In order to be an effective bioagent, endospores must be concentrated. Because bacterial endospores are not commonly found in nature, their ambient concentration is extremely low. As a result, the concentration of these endospores in poisoned mail is very high and a large quantity of endospores in a piece of mail is very likely to represent a bioattack involving anthrax, tetanus, gas gangrene or botulism. Therefore, a device and method that allows for the fast and specific detection of endospores without opening the mail or, at the very least, that only creates a small puncture or cut in the mail that can be rapidly sealed so that the bacteria either never leave the mail or are deposited in an aerosol concentrator would be an important improvement in the art.

SUMMARY OF THE INVENTION

A device for detecting bacterial endospores in a sealed container is provided. The device has a suction tube connected to an aerosol concentrator containing a lanthanide salt solution. A suction pump is engaged to the aerosol concentrator and an optical set-up directs the excitation energy source to the lanthanide salt solution and collects photoluminescence generated by the excited lanthanide salt solution.

A method for detecting bacterial endospores is also provided in which the sealed container is punctured. A suction tube connected to an aerosol concentrator is inserted into the puncture. The step of drawing air from inside the container through the puncture and into the aerosol concentrator is performed. The air drawn from the container is deposited into a lanthanide salt solution and the salt solution is excited with an excitation energy source. Emissions from at least one lanthanide salt emission band are collected and photoluminescence in the emissions from the lanthanide salt in the solution are measured.

A device for detecting bacterial endospores in a sealed container in which a lanthanide salt solution capable of being injected into the sealed container is provided. The device has a set of optical fibers that detects an excitation energy source to the lanthanide salt solution and collects photoluminescence emissions generated by the excited lanthanide salt.

DETAILED DESCRIPTION

A device for detecting bacterial endospores in a sealed container is provided. The device is comprised of a suction tube connected to an aerosol concentrator containing a lanthanide salt solution, a suction pump engaged to the aerosol concentrator, an excitation energy source and an optical set-up which directs the excitation energy source to the lanthanide salt solution and collects photoluminescence generated by the excited lanthanide salt solution.

A method is provided for detecting bacterial endospores inside a sealed container, with the method being comprised of the steps of puncturing the sealed container to form a puncture, inserting a suction tube connected to an aerosol concentrator into the puncture, drawing air from inside the container through the puncture and into the aerosol concentrator, depositing the air drawn from the container into a lanthanide salt solution, exciting the lanthanide salt solution with an excitation energy source, collecting emissions from a lanthanide salt emission band and measuring the photoluminescence in the emissions from the lanthanide salt in the solution.

In another embodiment, a lanthanide salt solution is injected through a puncture into the sealed container. Following the injection of the lanthanide salt solution, two sets of optical fibers are inserted into the container. Once this is done, the solution is excited with an ultraviolet light using one of the two sets of optical fibers. A second of the two sets of optical fibers is then used to collect photoluminescence emitted from the excited lanthanide salt solution. The collected photoluminescence are then measured to determine presence of bacterial endospores.

A device is also provided for detecting bacterial endospores in a sealed container where the device is comprised of a lanthanide salt solution capable of being injected into the sealed container, an excitation energy source and a set of optical fibers for directing the excitation energy source to the lanthanide salt solution and collecting photoluminescence emissions generated by the excited lanthanide salt.

Figure 1:
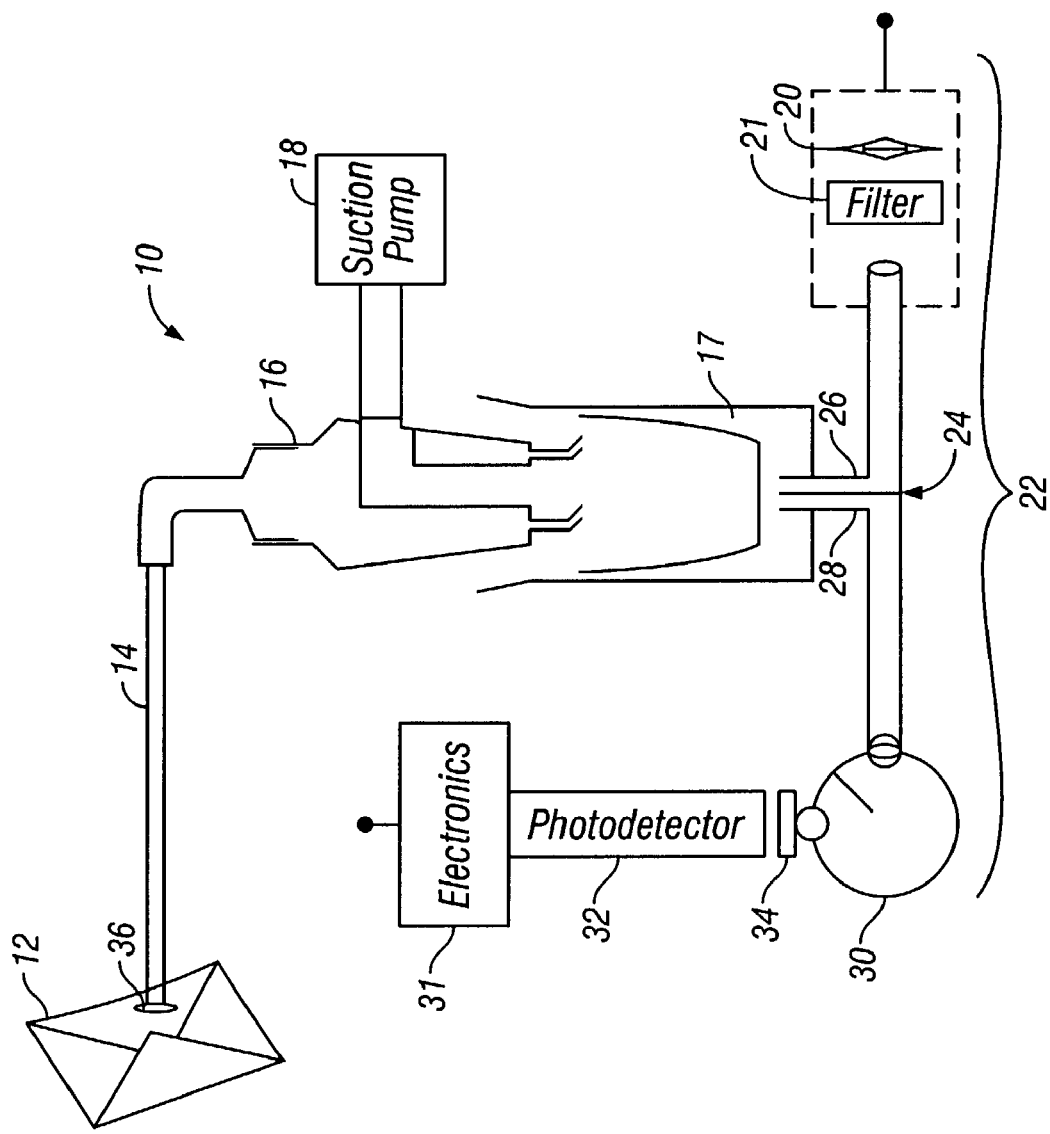
FIG. 1 is a schematic showing a device for the detection of endospores.

A device 10 for detecting bacterial endospores in a sealed container 12 is provided. As shown in FIG. 1, the device 10 is comprised of a suction tube 14 connected to an aerosol concentrator 16 containing a lanthanide salt solution, a suction pump 18 engaged to the aerosol concentrator 16, an excitation energy source 20 and an optical set-up 22 for directing the excitation energy source 20 to the lanthanide salt solution and collecting photoluminescence generated by the excited lanthanide salt solution.

The aerosol concentrator 16 used in conjunction with the device may selectively be a bubbler, impinger or an impactor-type concentrator. Furthermore, the excitation energy source 20 can be, among other things, an ultraviolet light, a pulsed xenon arc lamp, a pulsed laser or modulated light source. The excitation energy source may be used in conjunction with a filter 21, such as a broadband ultraviolet filter.

The optical set-up 22 seen in the example of FIG. 1 has a probe 24 having a first and a second optical fiber 26, 28 wherein the first optical fiber 26 excites the lanthanide salt solution with an ultraviolet light and a second optical fiber 28 collects an emission from one of the lanthanide emission bands generated by the lanthanide salt solution upon receipt of the excitation energy source. These emission may then be collected in an integrating sphere 30 where they can be measured using a photodetector 32 such as a photomultiplier with associated analyzing electronics 31. If necessary, a filter 34 (such as a narrow band filter at 540 nm) may be positioned between the integrating sphere 30 and the photomultiplier 32.

The lanthanide salt can be in various forms including, but not limited to, europium chloride and terbium chloride. The sealed container 12 may be, among other things, an envelope, a box and a package.

Suction tube 14 used to draw an air sample may selectively contain a sealing apparatus capable of sealing a small opening puncture 36 created when the sealed container 12 is punctured. The sealed container 12 may selectively be placed under a protective device such as a hood such that if the sealed container is opened up even a small amount, the contents will not be freely dispersed into the environment. Alternatively, the sealed container 12 may selectively be placed in a safety container such as a plastic bag having a plug that allows the probe 24 of the optical set-up 22 to be inserted into the sealed container 12. The safety container plug may selectively be resealed after examination. A plug may alternatively be placed at the end of an air sampler to allow the container to be resealed after examination.

The embodiment of FIG. 1 shows a device 10 where air is drawn from a puncture 36 in the container 12 into an aerosol concentrator 16 that contains a terbium chloride (TbCl$_3$) solution 17, and photoluminescence from terbium dipicolinate is measured in the concentrator. The device 10 removes air from a sealed container 12 and detects dipicolinic acid that comes from bacterial endospores. Once a puncture is made in the container 12, a tube 14 for air is inserted in the puncture. Air is drawn into the aerosol concentrator 16 which deposits the aerosol into a solution of terbium chloride 17. Probe 24 comprising two optical fibers 26, 28 excites the solution 17 with ultraviolet light. Optical fiber 28 collects emission from one of the terbium emission bands (for example a band may be at 540 nm). The photoluminescence is measured after a short delay relative to the excitation pulse. Bacterial endospores may be immediately detected inside the aerosol concentrator. The detected endospores may be available for serological or DNA analysis.

A method for detecting bacterial endospores inside a sealed container 12 is also provided where the method is comprises of the steps of: (a) puncturing the sealed container 12 to form a puncture 36; (b) inserting a suction tube 14 connected to an aerosol concentrator 16 into the puncture 36; (c) drawing air from inside the container 12 through the puncture 36 and into the aerosol concentrator 16; (d) depositing the air drawn from the container 12 into a lanthanide salt solution; (e) exciting the lanthanide salt solution with an excitation energy source 20; (f) collecting emissions from at least one lanthanide salt emission band; and (g) measuring the photoluminescence in the emissions from the lanthanide salt in the solution.

In one embodiment of the method, the excitation energy source 20 is an ultraviolet light. The ultraviolet light may be transmitted by, among other things, a modulated light source, a pulsed xenon arc lamp and a pulsed laser. The lanthanide salt solution used may be in several forms including, but not limited to, terbium chloride and europium chloride.

The lanthanide salt solution may selectively be excited with an ultraviolet light using a first optical fiber 26 of a probe 24 having at least two optical fibers 26, 28. In this embodiment, second optical fiber 28 collects emission from one of the lanthanide salt solution emission bands. The sealed container 12 used may be any type including, but not limited to, an envelope, a box and a package.

A method is provided for detecting bacterial endospores inside a sealed container 12 where a lanthanide salt solution is injected into the sealed container 12 through the puncture 36. Following the injection of the lanthanide solution, two sets of optical fibers 26, 28 are inserted into the container 12. Once this is done the lanthanide solution is excited with an ultraviolet light 20 using one of the two sets of optical fibers 26, 28. The photoluminescence emitted from the excited lanthanide salt solution is then collected using the second of the two sets of optical fibers 26, 28. The collected photoluminescence is then measured to detect the presence of dipicolinic acid.

Again, the lanthanide salt used in the method can be, among other things, terbium chloride or europium chloride. Also, the light is transmitted by one of several sources 20 including, but not limited to, a modulated light source, a pulsed xenon arc lamp and a pulsed laser.

The solution is excited with ultraviolet light using a first optical fiber 26 of a probe 24 having at least two optical fibers 26, 28. In this embodiment, a second optical fiber 28 collects emission from one of the lanthanide salt solution emission bands. As mentioned above, the sealed container 12 can be in several forms, including an envelope, a box and a package.

Figure 2:
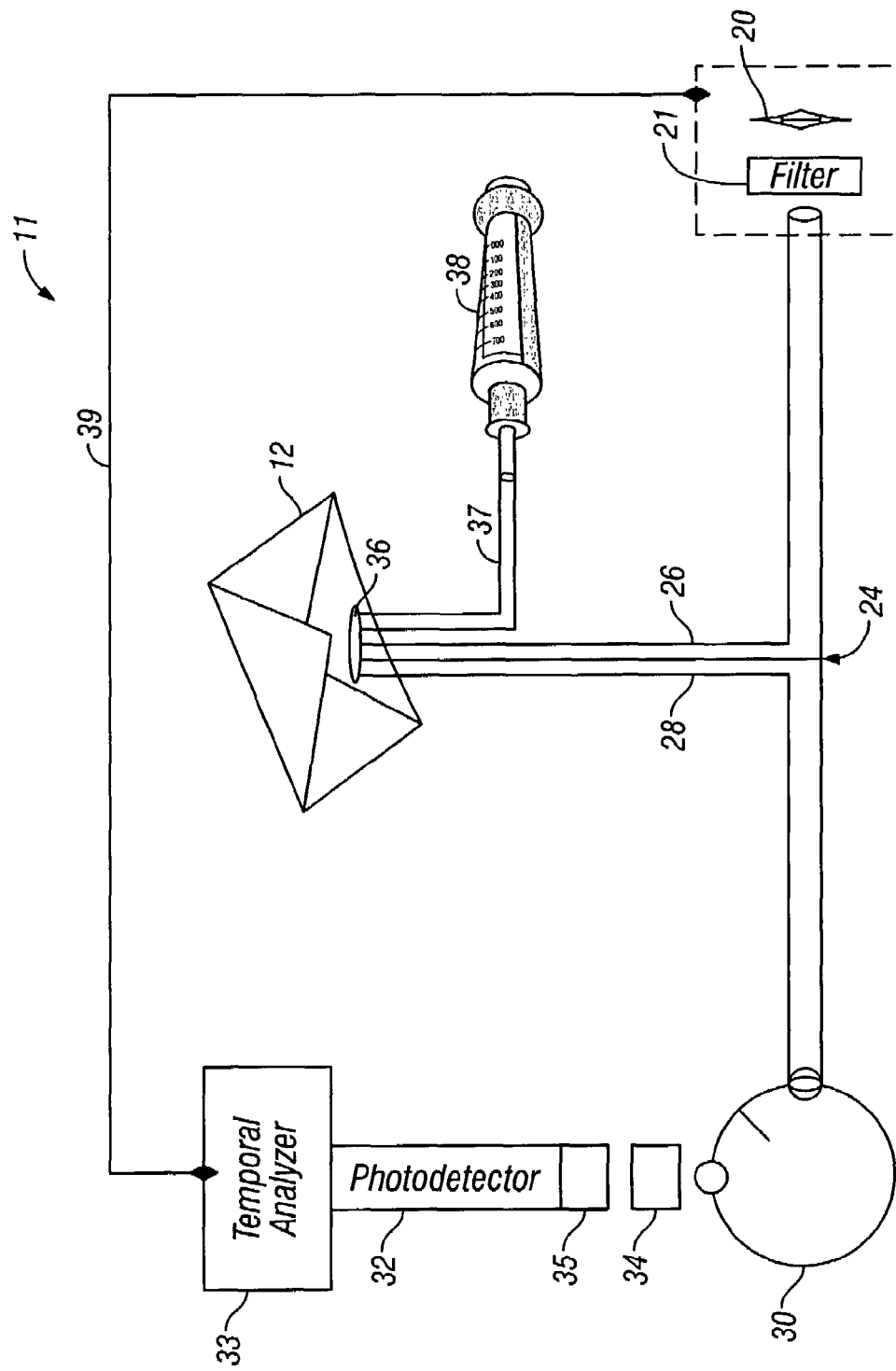
FIG. 2 is a schematic showing an alternative device for injecting a lanthanide salt solution into a sealed container in order to detect endospores in the container.

An alternative embodiment is provided in FIG. 2 for detecting bacterial endospores in a sealed container 12 with a device 11 utilizing a lanthanide salt solution capable of being injected into the sealed container 12. The device comprising an excitation energy source and a set of optical fibers 26, 28 for directing the excitation energy source 20 to the lanthanide salt solution and collecting photoluminescence emissions generated by the excited lanthanide salt. A broadband ultraviolet filter 21 may selectively be used with the excitation energy source 20.

The excitation energy source 20 may selectively be an ultraviolet light. In the embodiment of FIG. 2, the lanthanide salt solution may be contained in a squeezable tube 38. Again, the lanthanide solution can be in several forms, including terbium chloride or europium chloride. In still another embodiment, the lanthanide salt solution is in a sol-gel applied to the set of optical fibers 26, 28.

In the device 11 of FIG. 2, a terbium chloride solution through a tube 37 is injected into the sealed container 12 and photoluminescence from terbium dipicolinate is measured while it is inside the container. The device 11 of FIG. 2 detects dipicolinic acid that may come from bacterial endospores without removing any material from the container 12. A tube 38 for injecting terbium chloride solution is inserted into the puncture 36 and a forward and backscattering probe 24 having two sets of optical fibers 26, 28 is also inserted into the puncture. One optical fiber 26 adds UV light to excite photoluminescence, and optical fiber 28 collects photoluminescence for analysis.

The photoluminescence from optical fiber 28 is carried to a collection device 30 (such as an integrating sphere) and a photodetector 32 measures the intensity of the emission with signaling sent from the photodetector to a temporal analyzer 33. The photodetector (such as a photomultiplier tube in one example) may operate with a narrow band filter 34 (for instance a 540 nm filter). The temporal analyzer 33 (FIG. 2) and excitation energy source 20 are coupled together and communication is made by an electronic trigger 39. In the device 11 of FIG. 2, bacterial endospores may be detected while inside the container without removing the endospores.

Ultraviolet (UV) radiation illuminates the contents of the sealed container 12. An example of a sealed container 12 is a cardboard box or envelope; an example of a UV source is an arc lamp. The light emitted from the contents is collected by another optical fiber 28 and passed on to an optical collection device. Examples of collection devices 30 would be a lens, an integrating sphere, or a fiber optic.

The light then may selectively pass through a dispersive device 34 that selects a wavelength that is characteristic of the lanthanide salt. An example of a lanthanide can be terbium or europium, an example of a dispersive device 34 is a narrow band filter or a spectrometer, and an example of an emission band is the 542 nm band in terbium salts. A photodetector 32 measures the intensity of emission as a function of time before and after excitation. Examples of photodetectors 32 include photomultipliers, photodiodes and charge coupled diode arrays. The signal from the photodetector is sent to a temporal analyzer 33. Examples of temporal analyzers: a digital oscilloscope, a multichannel analyzer, and an A/D converter attached to a computer. The temporal analyzer 33 analyzes the temporal profile of the emitted light. An example of such an analysis is the determination of emission lifetime, the measurement of peak intensity, the measurement of time integrated intensity, or phase modulation.

The wavelength dispersive device 34 and the temporal analyzer 33 are employed since many aerosols emit light by photoluminescence. Isolating the terbium dipicolinate emission from the species is important to eliminate false positive detections. As an example, terbium dipicolinate has a strong a narrow emission band a wavelength 542 nm, and in the presence of a surplus of terbium, lifetime of 0.6 ms.

While the principles of the invention have been shown and described in connection with but a few embodiments, it is to be understood clearly that such embodiments are by way of example and are not limiting.

We claim:

1. A method for detecting bacterial endospores inside a sealed container, the method comprising of the steps of:
   puncturing the sealed container;
   injecting a lanthanide salt solution into the container through the puncture;
   inserting two sets of optical fibers into the container;
   exciting the solution with an ultraviolet light using one of the two sets of optical fibers;
   collecting photoluminescence emitted from the excited lanthanide salt solution with a second of the two sets of optical fibers; and
   measuring the photoluminescence from the lanthanide salt in the solution.

2. The method of claim 1 wherein the lanthanide salt is terbium chloride.

3. The method of claim 1 wherein the lanthanide salt is europium chloride.

4. The method of claim 1 wherein the light is transmitted by one of (a) a modulated light source, (b) a pulsed xenon arc lamp, and (c) a pulsed laser.

5. The method of claim 1 further comprising exciting the solution with ultraviolet light using a first optical fiber of a probe having at least two optical fibers.

6. The method of claim 1 further comprising collecting emission from one of the lanthanide salt solution emission bands with a second optical fiber.

7. The method of claim 1 wherein the sealed container is one of: (a) an envelope, (b) a box, and (c) a package.

* * * * *